United States Patent [19]

Cuthbertson

[11] 4,237,321

[45] Dec. 2, 1980

[54] 2,4,5-TRICHLOROPHENOL PROCESS

[75] Inventor: Eric Cuthbertson, Newcastle upon Tyne, England

[73] Assignee: Sterling Drug Inc., New York, N.Y.

[21] Appl. No.: 966,101

[22] Filed: Dec. 4, 1978

[30] Foreign Application Priority Data

Dec. 6, 1977 [GB] United Kingdom ............... 50773/77

[51] Int. Cl.$^2$ ........................ C07C 39/32; C07C 37/00
[52] U.S. Cl. ..................................... 568/776; 568/776
[58] Field of Search ................................. 568/779, 776

[56] References Cited

U.S. PATENT DOCUMENTS

| | | | |
|---|---|---|---|
| 2,494,993 | 1/1950 | Foster | 568/779 |
| 2,665,314 | 1/1954 | Krantz | 568/776 |
| 3,318,949 | 5/1967 | Roberts | 568/779 |

FOREIGN PATENT DOCUMENTS

| | | | |
|---|---|---|---|
| 527393 | 6/1929 | Fed. Rep. of Germany | 568/779 |
| 197547 | 7/1967 | U.S.S.R. | 568/779 |

OTHER PUBLICATIONS

Groves, et al. "Journal of the Chemical Society", (1929), pp. 512–513.
Galat, "Journal of the American Chemical Society", (1952), 74 pp. 3890–3891.
Merck Index 9th Ed., Merck Co., Inc. pp. 4546, 9322 & 9324 (1976).

*Primary Examiner*—Werren B. Lone
*Attorney, Agent, or Firm*—Theodore C. Miller; B. Woodrow Wyatt

[57] ABSTRACT

A method of making 2,4,5-trichlorophenol by chlorinating 2,5-dichlorophenol is characterized by reacting 2,5-dichlorophenol with chlorine in the presence of a liquid inert polar aprotic reaction medium such as nitrobenzene or a chlorinated hydrocarbon reaction medium, particularly 1,2-dichloroethane, and preferable a Lewis acid catalyst, particularly aluminium chloride. The product contains a higher ratio of 2,4,5-trichlorophenol to 2,3,6-trichlorophenol than has been obtainable previously.

9 Claims, No Drawings

2,4,5-TRICHLOROPHENOL PROCESS

This invention relates to a new method of making 2,4,5-trichlorophenol, a valuable intermediate. Reacted with chloroacetic acid, this compound gives rise to 2,4,5-trichlorophenoxyacetic acid (245-T) a widely used herbicide. By reacting the subject intermediate with formaldehyde, one obtains hexachlorophene (2,2'-dihydroxy-3,5,6,3',5',6'-hexachlorodiphenylmethane) widely used as a germicide, especially in soaps and cosmetics.

Hitherto, 2,4,5-trichlorophenol has been manufactured on a commercial scale by the hydrolysis of 1,2,4,5-tetrachloro-benzene, using sodium hydroxide in methyl alcohol under pressure at a temperature of 150° to 180° C. This is a hazardous reaction, since highly toxic 2,3,7,8-tetrachloro-p-dibenzodioxin can be formed as a by-product and if very critical reaction conditions are not maintained an uncontrolled rise in temperature can occur accompanied by greatly increased formation of this by-product. The recent disaster at Seveso in Italy where a large area of land was rendered unusable was a result of this process. Consequently, there is a need for a new and safer process.

It is also known to make 2,4,5-trichlorophenol by the chlorination of 2,5-dichlorophenol. This process was described by L. G. Groves, E. E. Turner and G. I. Sharp in the Journal of the Chemical Society (1929) pages 512 to 524; and again by A. Galat in the Journal of the American Chemical Society (1952), 74, pages 3890 and 3891; both using acetic acid as the reaction medium. The difficulty with this reaction is that 2,3,6-trichlorophenol is formed as an unwanted by-product, which is difficult to separate from the 2,4,5-trichlorophenol. The reaction may be illustrated thus:

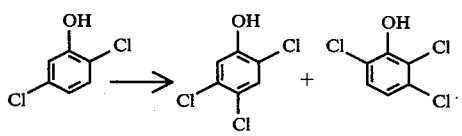

It is desirable in this reaction that the ratio of 2,4,5-trichlorophenol to 2,3,6-trichlorophenol formed should be as high as possible. Various alterations of the reaction conditions have been tried, in order to achieve a high ratio, but none has been really successful. The present invention arises from our discovery of reaction conditions which achieve a substantially higher ratio than previously.

The invention provides a method of making 2,4,5-trichlorophenol, which method comprises reacting 2,5-dichlorophenol with chlorine in the presence of a liquid inert polar aprotic reaction medium, and, when the reaction medium has a dielectric constant below 30, a Lewis acid catalyst.

2,5-dichlorophenol is a known compound. It can be made from the cheaply available 2,5-dichloroaniline by the known steps of diazotisation followed by hydrolysis. These steps and also the chlorination of the 2,5-dichlorophenol, can readily be carried out under conditions which avoid the possibility of forming 2,3,7,8-tetrachloro-dibenzo-p-dioxin.

A very important advantage of this method is the fact that 2,4,5-trichlorophenol so made by this process does not contain any 2,3,7,8-tetrachloro-p-dibenzodioxin, provided that the 2,5-dichlorophenol is also dioxin-free. Therefore, the method eliminates the very big risk associated with the prior process involving the hydrolysis of 1,2,4,5-tetrachlorobenzene.

The reaction medium is inert to the other components of the reaction mixture and is liquid under the reaction conditions, so as to hold the reactants in solution. The medium is polar, the more so the better from the view point of improving reaction efficiency, and preferably has a dielectric constant of at least 8. The reaction medium should be aprotic because solvents containing reactive hydrogen will normally react with other components of the reaction mixture and interfere with the desired chlorination reaction. Our preferred reaction medium is nitrobenzene, a compound having a dielectric constant at 25° C. of 35. Other suitable reaction media include chlorinated hydrocarbons which may be aliphatic, alicyclic, or aromatic such as chlorobenzene. Preferred compounds are dichloromethane (dielectric constant 8.93), and particularly 1,2-dichloroethane (dielectric constant 10.5). The amount of this reaction medium used is not critical. Enough should be used to dissolve the reactants; when the solvent needs to be removed by evaporation after the reaction, no more should be used than necessary. Generally, one to five parts by weight of inert reaction medium per part by weight of 2,5-dichlorophenol will be appropriate.

A Lewis acid catalyst is necessary for efficient performance of the invention when the dielectric constant of the organic reaction medium is less than 30. Though such catalyst is not strictly necessary when the dielectric constant of the organic reaction medium is greater than 30, a catalyst always improves the proportion of 2,4,5-trichlorophenol obtained, and its presence is always preferred.

The nature of the Lewis acid catalyst is not critical. As suitable materials there may be mentioned aluminium chloride, aluminium bromide, zinc chloride, boron trifluoride etherate, titanium tetra-chloride, stannic chloride and antimony pentachloride. Aluminium chloride is preferred. The catalyst should be used in an amount of from 0.5% to 10% by weight on the weight of the 2,5-dichlorophenol. Though these figures are not critical, little catalytic effect is observed with amounts of catalyst below 0.5%, and little or no advantage is gained by using 10% catalyst over 4%.

The reaction is preferably performed at a temperature from −10° C. to reflux, particularly from 0° C. to +20° C. It is believed that low temperatures may favour formation of the desired 2,4,5-isomer, at the expense of the 2,3,6-isomer. On the other hand, solubility of the reactants in the reaction medium is reduced at low temperatures so that large amounts of reaction medium may need to be used to avoid risk of blocking the chlorine inlet.

The reaction may conveniently be performed by providing the 2,5-dichlorophenol, the organic reaction medium and the Lewis acid catalyst in a reaction vessel, and slowly metering in the required amount of chlorine. The desired reaction takes place rapidly. It is preferred to use about a stoichiometrically equivalent amount of chlorine, for the use of too little chlorine leaves unchanged 2,5-dichlorophenol in the reaction mixture and the use of too much chlorine results in the formation of 2,3,4,6-tetrachlorophenol. The reaction mixture may be worked up by the addition of water or aqueous hydrochloric acid to destroy the excess Lewis acid catalyst. The reaction mixture is then filtered to remove any insoluble material, and the two immiscible layers separated. The 2,4,5-trichlorophenol may be used as it is in solution, or may be recovered as a solid by known techniques. Thus, if it is sufficiently volatile (and chlorinated aliphatic hydrocarbons generally are), the reaction medium may simply be evaporated off. If the reaction medium is not sufficiently volatile for this, the 2,4,5-trichlorophenol may be extracted into aqueous alkali, precipitated by acidification and recovered by filtration and/or further organic solvent extraction.

The following Examples illustrate the invention.

EXAMPLE 1

120 g of 2,5-dichlorophenol was dissolved in 250 ml of dry 1,2-dichloroethane and the solution cooled to 12° C.

4.8 g of anhydrous aluminium chloride was added and the mixture stirred for 10 minutes at 12° C. 52.3 g of chlorine was then added, with stirring, over a period of 3–4 hours and the mixture was then stirred for a further ½ hour. The temperature was maintained between 12° and 14° throughout.

10 ml of 37% hydrochloric acid was added, the mixture stirred for 10 minutes, filtered and the solvent distilled off. 143 g of product was obtained, which contained (as determined by glc analysis) 89–90% 2,4,5-trichlorophenol, 7% 2,3,6-trichlorophenol, 2–3% 2,3,4,6-tetrachlorophenol and >1% 2,5-dichlorophenol and other impurities. The ratio of 2,4,5-trichlorophenol to 2,3,6-trichlorophenol was thus 12.8:1.

EXAMPLES 2 to 25

There are three features which are critical to the success of this invention; a liquid inert polar aprotic reaction medium; where the dielectric constant of the reaction medium is not greater than 30, a Lewis acid catalyst; and the use of free, rather than combined, chlorine as the chlorinating agent. Using these three features in combination, we are able to achieve a ratio of 2,4,5-trichlorophenol to 2,3,6-trichlorophenol of at least 6:1 and generally of more than 10:1. Our attempts to repeat the prior art process have resulted in product mixtures with a ratio below 6:1. Moreover, the use of any two of the above noted critical features without the third does not appear to give any improvement over the prior art. It is therefore surprising that three critical features together give such good results. These facts are illustrated by the experiments of Examples 2 to 16 reported in the Tables below. Table 1 shows the reagents and reactions conditions employed, and Table 2 the product distribution. Examples 11, 12, 13, 15 and 16 are in accordance with the present invention; the others are included for purposes of comparison.

Examples 17 to 25 are comparable to Nos. 1 to 16 and show the effect of varying the reaction medium and the Lewis acid catalyst. Reaction conditions are set out in Table 3 and results in Table 4.

TABLE 1

| | Reagents and Reaction Conditions | | | | |
|---|---|---|---|---|---|
| Example | Chlorinating Agent | Medium (wt/wt DCP) | Catalyst (wt % DCP) | Temp °C. | Time (hr) |
| 2 | Cl₂ | AcOH (4 pts) | — | 9–10 | 3.5 |
| 3 | Cl₂ | EDC (5 pts) | — | 10–15 | 3.5 |
| 4 | Cl₂ | AcOH (1 pt) | — | 8 | 1.8 |
| 5 | Cl₂ | — | — | 65 | 4.75 |
| 6 | Cl₂ | AcOH (2 pts) | KOAc (60%) | 7 | 1 |
| 7 | SO₂Cl₂ | EDC (2.5 pts) | silica gel | 15–20 | 24 |
| 8 | SO₂Cl₂ | EDC (2.5 pts) | AlCl₃ (1.2%) (100%) | 15–20 | 24 |
| 9 | SO₂Cl₂ | EDC (2.5 pts) | — | 15–20 | 24 |
| 10 | Cl₂ | AcOH (1.2 pts) | AlCl₃ (2.5%) | 3–5 | 1 |
| 11 | Cl₂ | EDC (2.5 pts) | AlCl₃ (3%) | 5–6 | 0.75 |
| 12 | Cl₂ | EDC (2.5 pts) | AlCl₃ (5%) | 9–11 | 4 |
| 13 | Cl₂ | EDC (2.5 pts) | AlCl₃ (10%) | 9–10 | 6 |
| 14 | Cl₂ | Hexane (3 pts) | AlCl₃ (3%) | 15–20 | 1 |
| 15 | Cl₂ | Dichloromethane (2.5 pts) | AlCl₃ (4%) | 8–12 | 3.6 |
| 16 | Cl₂ | EDC (2.5 pts) | AlCl₃ (4%) | 12–14 | 3 |

DCP is 2,5-dichlorophenol
AcOH is acetic acid
EDC is 1,2-dichloroethane

TABLE 2

| | Product Distributions | | | | |
|---|---|---|---|---|---|
| Example | %-2,5 DCP | % 2,3,6-TCP | % 2,4,5-TCP | % 2,3,4,6-TCP | 2,4,5:2,3,6 ratio |
| 2 | 0.5 | 18.8 | 75.9 | 4.2 | 4.0:1 |
| 3 | 0.6 | 19.8 | 72.6 | 7.0 | 3.7:1 |
| 4 | 0.6 | 21.7 | 75.0 | 1.9 | 3.5:1 |
| 5 | 22.7 | 13.1 | 64.2 | — | 4.9:1 |
| 6 | 48.6 | 20.4 | 30.2 | — | 1.5:1 |
| 7 | 10.6 | 20.2 | 69.3 | — | 3.4:1 |
| 8 | 89.9 | 1.3 | 5.8 | — | 4.5:1 |
| 9 | 83.7 | 3.5 | 11.7 | — | 3.3:1 |
| 10 | 0.4 | 16.6 | 74.5 | 8.3 | 4.5:1 |
| 11 | 1.6 | 4.9 | 93.5 | — | 19:1 |
| 12 | 0.2 | 5.9 | 87.8 | 6.0 | 15:1 |
| 13 | 1.0 | 7.0 | 87.5 | 4.3 | 12.5:1 |
| 14 | 43.3 | 13.6 | 43.1 | — | 3.2:1 |
| 15 | 22.6 | 8.1 | 69.3 | — | 8.6:1 |
| 16 | 0.5 | 5.9 | 91.5 | 2.0 | 15.5:1 |

TABLE 3

| | Reagents and Reaction Conditions | | | | |
|---|---|---|---|---|---|
| Example | Medium Wt/Wt DCP | Dielectric Constant | Catalyst (Wt % DCP) | Temp °C. | Time Hr |
| 17 | EDC (2.5) | 10.5 | TiCl₄ (5.6) | 12–14 | 3.0 |
| 18 | EDC (2.5) | 10.5 | SnCl₄ (7.9) | 12–14 | 2.0 |
| 19 | EDC (2.0) | 10.5 | BF₃·Et₂O (4.3) | 12–14 | 2.0 |
| 20 | EDC (2.5) | 10.5 | ZnCl₂ (4.1) | 12–14 | 1.7 |
| 21 | Chlorobenzene (2.2) | 5.53 | AlCl₃ (4.0) | 12–14 | 1.6 |
| 22 | Chloroform (3.0) | 4.8 | AlCl₃ (4.0) | 12–14 | 1.6 |
| 23 | 1,1,2,2-Tetrachloroethane (3.2) | 8.2 | AlCl₃ (4.0) | 12–14 | 2.0 |
| 24 | Nitrobenzene (2.4) | 34.82 | AlCl₃ (4.0) | 15–20 | 2.0 |
| 25 | Nitrobenzene | 34.82 | — | 15–20 | 1.6 |

In all cases, chlorine was the chlorinating agent and the catalyst was charged in the same molar ratio.

TABLE 4

| | Product Distributions | | | | |
|---|---|---|---|---|---|
| Example | %2,5-DCP | %2,3,6-TCP | %2,4,5,-TCP | %2,3,4,6,-Tetra CP | 2,4,5:2,3,6, Ratio |
| 17 | 1.8 | 8.4 | 88.3 | 1.5 | 10.5:1 |
| 18 | 2.5 | 8.7 | 86.5 | 2.3 | 9.9:1 |
| 19 | 0.9 | 8.4 | 87.8 | 2.9 | 10.4:1 |

TABLE 4-continued

| | Product Distributions | | | | 2,4,5: |
| Example | %2,5-DCP | %2,3,6-TCP | %2,4,5,-TCP | %2,3,4,6,-Tetra CP | 2,3,6, Ratio |
| --- | --- | --- | --- | --- | --- |
| 20 | 2.3 | 8.7 | 86.1 | 2.9 | 9.9:1 |
| 21 | 1.4 | 10.5 | 84.9 | 3.2 | 8.1:1 |
| 22 | 1.4 | 10.2 | 84.8 | 3.6 | 8.3:1 |
| 23 | 0.4 | 7.5 | 87.9 | 4.1 | 11.7:1 |
| 24 | 0.4 | 4.3 | 92.6 | 2.6 | 21.5:1 |
| 25 | 4.6 | 6.6 | 87.5 | 1.4 | 13.5:1 |

I claim:

1. A method of making 2,4,5-trichlorophenol by chlorinating 2,5-dichlorophenol, characterized by reacting, at a temperature in the range from about −10° C. to about the reflux temperature of the reaction mixture, 2,5-dichlorophenol with about a stoichiometrically equivalent amount of chlorine in the presence of from about one to about five parts by weight of a liquid inert polar aprotic reaction medium having a dielectric constant from about 8 to about 35, and, when the reaction medium has a dielectric constant below 30, from about 0.5% to about 10% by weight of a Lewis acid catalyst based on the weight of the 2,5-dichlorophenol.

2. A method as claimed in claim 1, wherein the inert reaction medium is nitrobenzene.

3. A method as claimed in claim 1, wherein the inert reaction medium is a chlorinated hydrocarbon.

4. A method as claimed in claim 3, wherein the chlorinated hydrocarbon is 1,2-dichloroethane.

5. A method as claimed in any one of claims 1 to 3, wherein from one to five parts by weight of inert reaction medium are used per part by weight of 2,5-dichlorophenol.

6. A method as claimed in claim 1 wherein the Lewis acid catalyst is aluminium chloride.

7. A method as claimed in claim 1 wherein the Lewis acid catalyst is used in an amount of from 0.5% to 10% by weight on the weight of the 2,5-dichlorophenol.

8. A method as claimed in claim 1 wherein the reaction is performed by providing the 2,5-dichlorophenol, the inert reaction medium and the Lewis acid catalyst in a reaction vessel and slowly metering in the chlorine.

9. A method as claimed in claim 1 wherein the inert reaction medium is selected from the group consisting of 1,2-dichloroethane, dichloromethane, 1,1,2,2-tetrachloroethane and nitrobenzene.

* * * * *